United States Patent [19]

McNiff

[11] Patent Number: 4,613,716
[45] Date of Patent: Sep. 23, 1986

[54] PRODUCTION OF AROMATICS FROM ETHANE AND/OR ETHYLENE

[75] Inventor: Timothy K. McNiff, Weybridge, England

[73] Assignee: The British Petroleum Company p.l.c., London, England

[21] Appl. No.: 788,338

[22] Filed: Oct. 17, 1985

[30] Foreign Application Priority Data

Nov. 16, 1984 [GB] United Kingdom ............... 8429007

[51] Int. Cl.⁴ ............................................. C07C 12/02
[52] U.S. Cl. .................................... 585/415; 585/417
[58] Field of Search ................................ 585/415, 417

[56] References Cited

U.S. PATENT DOCUMENTS

| | | | |
|---|---|---|---|
| 4,056,575 | 11/1977 | Gregory et al. | 585/417 |
| 4,350,835 | 9/1982 | Chester et al. | 585/417 |
| 4,490,569 | 12/1984 | Chu et al. | 585/415 |
| 4,497,970 | 2/1985 | Young | 585/417 |

*Primary Examiner*—Curtis R. Davis
*Attorney, Agent, or Firm*—Brooks, Haidt, Haffner & Delahunty

[57] ABSTRACT

This invention relates to a process for producing aromatic hydrocarbons by bringing a feedstock containing at least 10% w/w of $C_2$ hydrocarbons into contact with a catalyst composition comprising a gallium loaded zeolite and a Group VIIB or Group VIII metal compound. The reaction is carried out at a temperature from 500°–750° C. A WHSV of 0.2–10 and a pressure of 1–20 bar are preferred. The presence of Group VIIB or Group VIII metal compounds increases conversion of the $C_2$ feed and reduces formation of undesirable polynuclear aromatics.

11 Claims, No Drawings

PRODUCTION OF AROMATICS FROM ETHANE AND/OR ETHYLENE

The present invention relates to a process for producing aromatic hydrocarbons from a hydrocarbon feedstock rich in $C_2$ hydrocarbons.

Hitherto synthetic routes to producing aromatics from open chain hydrocarbons have started from feedstocks which have at least three carbon atoms. Such feedstocks are initially dimerised and the dimerised product is subsequently cyclised over a variety of catalysts at temperatures in the region of 500°–600° C. Such processes are described for example in our British Pat. Nos. 1507778 and 1561590. According to the British Pat. No. 1561590 a gallium catalyst supported on an aluminosilicate in which the ratio of silica to alumina is between 20:1 and 70:1 is used.

Our published EP 0050021 discloses a process for producing aromatics from $C_2$ hydrocarbons, especially ethane, by bringing the hydrocarbon feed into contact with a gallium/zeolite catalyst at elevated temperature.

It has now been found that by incorporating into the gallium/zeolite catalyst small amounts of a Group VIIB or a Group VIII metal the activity of the catalyst for the conversion of $C_2$ hydrocarbons is substantially increased in terms of (a) increased conversion at a given temperature, or (b) achieving a given conversion at a lower temperature than used hitherto, and (c) reduction in the formation of undesirable polynuclear aromatics in the process.

Accordingly, the present invention is a process for producing aromatic hydrocarbons comprising bringing into contact in the vapour phase at a temperature from 500° C. to 750° C. a hydrocarbon feedstock containing at least 10% by weight of $C_2$ hydrocarbons with a catalyst composition comprising (i) an aluminosilicate loaded with gallium as a gallium compound and/or as gallium ions and having a silica to alumina molar ratio of at least 5:1, and (ii) a compound of a metal from Group VIIB or Group VIII of the Periodic Table.

The Periodic Table referred to herein and throughout the specification is the Table at pages 448 and 449 of the Handbook of Chemistry and Physics, 44th Edition, Ed. Hodgman, C. D. et al and published by The Chemical Rubber Publishing Co., Ohio, USA.

The $C_2$ hydrocarbon in the feedstock may be ethane, ethylene or mixtures thereof. The feedstock may contain in addition other open chain hydrocarbons containing between 3 and 8 carbon atoms as coreactants or a diluent which is inert under the reaction conditions. Specific examples of such additional coreactants are propane, propylene, n-butane, isobutane, n-butenes and isobutene. The hydrocarbon feedstock contains at least 10%, suitably at least 50%, preferably at least 70% by weight of $C_2$ hydrocarbons.

The aluminosilicate may be loaded with gallium by methods well known to those skilled in the art. Such methods are described for instance in our published EP-A-24930. Gallium is preferably present as gallium oxide in the catalyst composition.

The aluminosilicates loaded with gallium are preferably zeolites of an MFI or MEL type structures (cf. "Chemical Nomenclature, and Formulation of Compositions, of Synthetic and Natural Zeolites," IUPAC yellow booklet, 1978, and zeolite structure types published by The Structure Commision of the International aeolite Association entitled "Atlas of Zeolite Structure Types", by Meier, W. M. and Olsen, D. H. (1978), distributed by Polycrystal Book Service, Pittsburgh, Pa, USA). The zeolites suitably have a silica to alumina ratio of between 20:1 and 150:1 and may be selected from zeolites of the general formula: $M_{2/n}O.Al_2O_3.ySiO_2.zH_2O$ wherein M is a cation which is a positively charged ion selected from a metal ion or an organic ion of valence n and a proton, y is an integer greater or an organic ion of valence n and a proton, y is an integer greater than 5 and z is from 0 to 40. The metal cation, M, is preferably an alkali metal or alkaline earth metal ion, preferably sodium or potassium ions. The organic cations may be represented by the formula $R^1R^2R^3R^4N^+$ or by an ion derived from the amine $R^1R^2R^3N$, the diamine $R^1R^2N(CH_2)_xNR^3R^4$ or pyrrolidine where $R^1R^2R^3$ and $R^4$ may be H, $CH_3$, $C_2H_5$, $C_3H_7$, $C_4H_9$ or $-CH_2CH_2OH$ and x equals 2, 3, 4, 5 or 6. A typical example of the MFI zeolite is ZSM-5 though other zeolites of the ZSM variety, for example ZSM-8, ZSM-11, ZSM-12 and ZSM-35 may also be used. These are extensively described in a number of publications including U.S. Pat. No. 3,970,544 (Mobil). These zeolites are ususally produced from a silica source, an alumina source, an alkali metal hydroxide and a nitrogen containing base as template. The nitrogen-containing base may be organic such as an alkanolamine, for example diethanolamine, or inorganic, e.g. ammonia. Zeolites made in this manner are described in our published EP-A-Nos. 0002899, 0002900 and 0030811. Zeolites derived by process of EP-A-30811 are preferred.

The compound of a metal from Group VIIB or Group VIII of the Periodic Table may also be incorporated into the catalyst composition by impregnation or ion-exchange. Specifically, the Group VIIB and Group VIII metals are preferably selected from rhenium and iridium and these may be present in the catalyst composition as the oxides or as the respective ions. These oxides or ions may be suitably provided from a solution e.g. aqueous solution, of the respective metal salt such as for instance rhenium trichloride, ammonium perrhenate or iridium tribromide. Alternatively the gallium loaded zeolite may be intimately mixed with a Group VIIB or Group VIII metal compound.

The aluminosilicate may be loaded with the compounds of gallium and the Group VIIB or Group VIII metal in either order or a mixture of the two compounds may be used for simultaneous loading of the aluminasilicate. It is preferable to load the aluminosilicate with the Group VIIB or Group VIII metal compound prior to loading with gallium.

Whichever method of catalyst preparation is used, the amount of gallium present in the catalyst compositions may vary for instance from 0.05 to 10% by weight of the total aluminosilicate in the catalyst composition. The gallium exchanged or impregnated zeolite thus obtained may be combined with a porous matrix, e.g. silica or alumina or other inorganic compositions to improve the mechanical strength of the catalyst.

The amount of Group VIIB or Group VIII metal present in the catalyst composition is suitably from 0.05 to 10%, preferably from 0.1 to 0.8% w/w of the total composition.

The catalyst composition may be activated prior to contact with the hydrocarbon feedstock. The activation may be carried out by heating the catalyst at a temperature from 400° C. to 650° C., preferably from 500° C. to 600° C. Activation may be carried out in an atmosphere of hydrogen, air, steam or a gas inert under the reaction conditions such as nitrogen but preferably in an atmosphere containing oxygen. The activation may be carried out in the reactor itself prior to the reaction. The catalyst composition is suitably used in a fixed bed, a moving bed or a fluidised bed.

The hydrocarbon feedstock is thereafter contacted in the vapour phase with the catalyst composition at a temperature from 500° to 750° C. preferably from 570° to 650° C. in an inert atmosphere in the absence of oxygen. The inert atmosphere may be provided by a gas inert under the reaction conditions such as nitrogen distillation.

The reaction is suitably carried out at a WHSV for the reaction of 0.2 to 10, preferably from 0.5 to 2.0.

The reaction pressure is suitably from 1–20 bar, preferably from 1–10 bar.

Any unreacted $C_2$ hydrocarbon feedstock e.g. ethane or ethylene is recovered from the reaction products and may be recycled to the reaction along with the fresh hydrocarbon feedstock to be aromatised.

The invention is further illustrated with reference to the following Examples and Comparative Tests.

In the Examples and Comparative Tests the following notations have been used:

| | |
|---|---|
| *LIQUIDS = | Benzene, Toluene, $C_8$, $C_9$ and $C_{10}$ aromatics, poly nuclear aromatics (mainly napthalenes) |
| **$A_6$-$A_{10}$ = | Benzene, Toluene, $C_8$, $C_9$, $C_{10}$ mononuclear aromatics |
| SELECTIVITIES QUOTED = | $\frac{\text{YIELD (PRODUCT)}}{\text{CONVERSION OF ETHANE FEED}} \times 100$ |
| WHSV | Weight Hourly Space Velocity |
| CT | Contact Time |

In the Examples and Comparative Tests the liquid products of the reaction were identified by on-line dual column GC using a POROPAK QS column for the gaseous products from hydrogen to aromatics and a OV101 silicone gum rubber (SGR) column for the aromatics.

EXAMPLE 1

A sample of an MFI type zeolite containing ammonium cations (zeolite prepared using ammonia as template according to the general process of our published EP-A-0030811) was contacted with an aqueous solution of $ReCl_3$. The mixture was dried under vacuum at 130° C.

The rhenium impregnated zeolite was then contacted with an aqueous solution of gallium nitrate and dried under vacuum at 130° C.

The gallium/rhenium impregnated zeolite was bound in an inert silica matrix by mixing with an equal weight of LUDOX AS 40 (Registered Trade Mark) colloidal silica to obtain a slurry which was dried at 100° C. to give a hard cake which was broken up and sieved to give coarse particles which passed through a standard 12 mesh sieve but were retained by a 30 mesh sieve. This gave a final catalyst composition containing 0.7% w/w Ga and 0.4% w/w Re.

6 ml of this catalyst composition was taken and then loaded into a vertical fixed bed reactor. The catalyst composition was contacted with nitrogen and the temperature of the reactor raised to 550° C. The catalyst composition was maintained under these conditions for 16 hours.

The catalyst composition was then contacted with $H_2$ at 600° C. for 2 hours prior to testing for ethane aromatisation by contacting with ethane at 625° C., 1 WHSV and 3 bar pressure (CT—7.6 secs).

| CONVERSION OF ETHANE Wt % | SELECTIVITY TO LIQUIDS Wt % | SELECTIVITY TO $A_6$-$A_{10}$ Wt % |
|---|---|---|
| 48.2 | 46.3 | 39.4 |

EXAMPLE 2

A sample of an MFI type zeolite containing ammonium cations (zeolite prepared using ammonia as template according to the general process of our published EP-A-0030811) was contacted with an aqueous solution containing both $ReCl_3$ and $Ga(NO_3)_3$. The mixture was dried under vacuum at 130° C.

The metal impregnated zeolite was bound in an inert silica matrix using LUDOX AS 40 (Registered Trade Mark) colloidal silica as in Example 1 above and sieved to give catalyst particles which passed through a standard 12 mesh sieve but were retained by a 30 mesh sieve.

This procedure gave a catalyst composition containing 0.8% w/w Ga and 0.4% w/w Re.

The catalyst composition was treated and tested for aromatisation of ethane at 625° C., 1 WHSV and 3 bar pressure (CT—7.4 secs) as in Example 1 above.

| CONVERSION OF ETHANE Wt % | SELECTIVITY TO LIQUIDS Wt % | SELECTIVITY TO $A_6$-$A_{10}$ Wt % |
|---|---|---|
| 52.0 | 44.5 | 23.0 |

EXAMPLE 3

A sample of an MFI type zeolite containing ammonium cations (zeolite prepared using ammonia as template according to the general process of our published EP-A-0030811) was contacted with an aqueous solution of $NH_4ReO_4$. The mixture was dried under vacuum at 130° C.

The rhenium impregnated zeolite was then contacted with an aqueous solution of $Ga(NO_3)_3$ and dried under vacuum at 130° C.

The gallium/rhenium impregnated zeolite was bound in an inert silica matrix as in Example 1 above and was sieved to give catalyst particles which passed through a standard 12 mesh sieve but were retained by a 30 mesh sieve.

This procedure gave a catalyst composition containing 0.75% w/w Ga and 0.4% w/w Re.

The catalyst composition was treated as in Example 1 above and tested for the aromatisation of ethane at 600° C., 1 WHSV and 3 bar pressure (CT 8.0 secs).

| CONVERSION OF ETHANE Wt % | SELECTIVITY TO LIQUIDS Wt % | SELECTIVITY TO $A_6$-$A_{10}$ Wt % |
|---|---|---|
| 41.0 | 49.0 | 38.7 |

EXAMPLE 4

A sample of an MFI type zeolite containing ammonium cations (zeolite prepared using ammonia as a template according to the general process of our published EP-A-0030811) was impregnated with aqueous ReCl$_3$ dried, impregnated with aqueous Ga(NO$_3$)$_3$, dried and finally bound in an inert silica matrix as in Example 1 above.

The catalyst composition contained 0.6% w/w Ga and 0.5% w/w Re.

The catalyst composition was treated as in Example 1 above and tested for the aromatisation of ethane at 600° C., 2.5 bar pressure, 1 WHSV (CT—6.5 secs).

After running the fresh catalyst for about 5 hours on stream, the used catalyst was regenerated in situ using an air/nitrogen mixture starting at 500° C. rising to 550° C. and the total regeneration time was 16-20 hours.

The regenerated catalyst was retested for ethane aromatisation under the same conditions as the fresh catalyst referred to above in this Example. The results with both fresh and regenerated catalysts are tabulated below:

| CATALYST | CONVERSION OF ETHANE (Wt %) | SELECTIVITY TO LIQUIDS (Wt %) | SELECTIVITY TO A$_6$-A$_{10}$ Wt % |
|---|---|---|---|
| Fresh | 39.4 | 33.7 | 33.6 |
| Regenerated | 36.3 | 55.0 | 53.5 |

EXAMPLE 5

A sample of an MFI type zeolite containing ammonium cations (zeolite prepared using ammonia as a template according to the general process of our published EP-A-0030811) was contacted with an aqueous solution of IrBr$_3$. The mixture was dried at 130° C. under vacuum.

The iridium impregnated zeolite was then contacted with an aqueous solution of gallium nitrate and dried under vacuum at 130° C.

The gallium/iridium impregnated zeolite was bound in an inert silica matrix as described in Example 1 above and sieved to give catalyst particles which will pass through a standard 12 mesh sieve but are retained by a 30 mesh sieve. This procedure gave a catalyst composition containing 0.5% w/w Ga and 0.3% w/w Ir.

The catalyst composition was treated as in Example 1 above and tested for the aromatisation of ethane at 625° C., 1 WHSV and 3 bar pressure (CT—7.7 sec).

| CONVERSION OF ETHANE Wt % | SELECTIVITY TO LIQUIDS Wt % | SELECTIVITY TO A$_6$-A$_{10}$ Wt % |
|---|---|---|
| 53.0 | 42.5 | 42.3 |

COMPARATIVE TEST 1

(Not according to the invention)

A sample of an MFI type zeolite as described in Examples 1-5 was contacted with an aqueous Ga(NO$_3$)$_3$ solution. The mixture was dried under vacuum at 130° C.

The gallium impregnated zeolite was bound in a silica matrix using LUDOX AS 40 (Registered Trade Mark) colloidal silica as described previously in Example 1 above and sieved to give catalyst particles which passed through a standard 12 mesh sieve but were retained by a 30 mesh sieve.

The final catalyst composition contained 0.7% w/w Ga. This was treated as in Example 1 above and tested for the aromatisation of ethane at 625° C., 1 WHSV, 3 bar pressure (CT—7.5 secs).

| CONVERSION OF ETHANE Wt % | SELECTIVITY TO LIQUIDS* Wt % | SELECTIVITY TO A$_6$-A$_{10}$** Wt % |
|---|---|---|
| 33.9 | 46.0 | 23.3 |

For ease of comparison the results in terms of liquid product distribution from Examples 1, 3 and 5, and Comparative Tests 1 and 2 are tabulated below.

COMPARATIVE TEST 2

(Not according to the invention)

A sample of an MFI type zeolite as described in Examples 1-5 was contacted with an aqueous solution of ReCl$_3$. The mixture was dried under vacuum at 130° C.

The rhenium impregnated zeolite was bound in a silica matrix using LUDOX AS 40 (Registered Trade Mark) colloidal silica as described previously in Example 1 above and sieved to give catalyst particles which passed through a standard 12 mesh sieve but were retained by a 300 mesh sieve.

The final catalyst composition contained 0.5% w/w Re.

The catalyst composition was treated as in Example 1 above and tested for the aromatisation of ethane at 625° C., 3 WHSV, 1 bar pressure (CT—7.1 secs).

| CONVERSION OF ETHANE Wt % | SELECTIVITY TO LIQUIDS* Wt % | SELECTIVITY TO A$_6$-A$_{10}$** Wt % |
|---|---|---|
| 34.5 | 37.5 | 36.8 |

ETHANE AROMATISATION
LIQUID PRODUCT DISTRIBUTIONS

| | Catalyst Composition | | | | |
|---|---|---|---|---|---|
| | Comp Test 1 | Comp Test 2 | Ex 1 | Ex 3 | Ex 5 |
| Benzene | 27.74 | 45.27 | | | |
| | | 49.70 | | | |
| | | 42.27 | | | |
| | | 66.59 | | | |
| Toluene | 16.65 | 36.56 | 27.02 | 28.47 | 28.59 |
| Ethylbenezene | 0.65 | 7.03 | 0.65 | 4.31 | 0.24 |
| Xylene | 3.33 | 1.14 | 4.81 | 1.74 | 3.35 |
| C$_9$+Mononuclear aromatics | 1.86 | 0.91 | 1.92 | 2.24 | 0.31 |
| C$_{10}$+Mononuclear aromatics | 0.37 | 7.03 | 0.23 | 0.35 | 0.30 |
| Naphthalene | 22.95 | 1.14 | 12.27 | 14.17 | 0.63 |
| Methylnaphthalene | 19.97 | 0.91 | 3.42 | 6.33 | — |
| Dimethyl naphthalene | 6.49 | — | — | 0.13 | — |

I claim:

1. A process for producing aromatic hydrocarbons, said process comprising bringing into contact in the vapour phase at a temperature from 500°-750° C. a hydrocarbon feedstock containing at least 10% by weight of C$_2$ hydrocarbons with a catalyst composition comprising (i) an aluminosilicate loaded with gallium as a gallium compound and/or as gallium ions and having a silica to alumina molar ratio of at least 5:1, and (ii) a compound of the metal rhenium or iridium.

2. A process according to claim 1 wherein the hydrocarbon feedstock contains at least 50% by weight of $C_2$ hydrocarbons.

3. A process according to claim 1 or 2 wherein the aluminosilicate loaded with gallium is an MFI or an MEL type zeolite.

4. A process according to claim 1 or 2 wherein the gallium, and the rhenium, or iridium metals are present in the catalyst as their respective oxides.

5. A process according to claim 1 or 2 wherein gallium is present in an amount from 0.05 to 10% by weight of the total catalyst composition.

6. A process according to claim 1 or 2 wherein the metal rhenium or iridium is present in an amount from 0.05 to 10% by weight of the total catalyst composition.

7. A process according to claim 1 or 2 wherein the catalyst composition is activated by heating at a temperature from 400° to 650° C. prior to contact with the hydrocarbon feedstock.

8. A process according to claim 1 or 2 wherein the hydrocarbon feedstock is brought into contact with the catalyst composition at a WHSV from 0.2-10 and a pressure from 1-20 bar.

9. A process according to claim 1 or 2 wherein unreacted $C_2$ hydrocarbons are recovered from the reaction products and are recycled along with the fresh hydrocarbon feedstock to be aromatised.

10. A process according to claim 1, wherein the metal is rhenium.

11. A process according to claim 1, wherein the metal is iridium.

* * * * *

UNITED STATES PATENT AND TRADEMARK OFFICE
CERTIFICATE OF CORRECTION

PATENT NO. : 4,613,716

DATED : September 23, 1986

INVENTOR(S) : Timothy Kevin McNiff

It is certified that error appears in the above-identified patent and that said Letters Patent is hereby corrected as shown below:

Col. 2, line 23 correct misspelled word "ususally" to read --usually--

Col. 5, line 16 change "in situ" to read --*in situ*--

Col. 6, line 44 insert the word --COMPONENTS-- as a heading above listed components Col. 6, line 48-50 move numbers "49.70", "42.27" and "66.59" under the heading of Comp Test and insert --49.70-- under the heading Ex 1; insert --42.27-- under the heading Ex 3; and insert --66.59-- under the heading Ex 5.

Col. 6, line 52 correct misspelled word "Ethylbenezene" to read --Ethylbenzene--.

Signed and Sealed this

Tenth Day of March, 1987

*Attest:*

DONALD J. QUIGG

*Attesting Officer*    *Commissioner of Patents and Trademarks*